United States Patent [19]

Epstein

[11] Patent Number: 4,650,470
[45] Date of Patent: Mar. 17, 1987

[54] PORTABLE WATER-JET SYSTEM

[76] Inventor: Harry Epstein, 687 Kildare Crescent, Seaford, N.Y. 11783

[21] Appl. No.: 719,259

[22] Filed: Apr. 3, 1985

[51] Int. Cl.⁴ ............................................ A61M 7/100
[52] U.S. Cl. ..................... 604/149; 604/275; 604/33; 604/85; 137/625.48; 239/310
[58] Field of Search ............... 239/310, 317, 318, 428; 604/275, 149, 30, 33, 82, 85, 131, 150, 155, 323, 902; 137/625.48

[56] References Cited

U.S. PATENT DOCUMENTS

| | | | |
|---|---|---|---|
| 2,603,217 | 7/1952 | McShirley | 604/275 X |
| 2,789,010 | 4/1957 | Dean | 239/310 |
| 2,849,208 | 8/1958 | Skipwith, Jr. | 239/318 |
| 3,060,956 | 10/1962 | Menzie | 239/310 |
| 3,227,380 | 1/1966 | Pinkston | 604/150 X |
| 3,254,647 | 6/1966 | Vogel | 239/317 |
| 3,367,353 | 2/1968 | Hunter | 239/310 |
| 3,667,683 | 6/1972 | Gilbert | 239/428.5 |
| 3,669,101 | 6/1972 | Kleiner | 604/150 X |
| 3,682,392 | 8/1972 | Kint | 239/428.5 |
| 3,690,565 | 9/1972 | Abos | 239/428.5 |
| 3,722,798 | 3/1973 | Bletcher et al. | 239/428.5 |
| 4,238,074 | 12/1980 | Coons | 239/310 |

Primary Examiner—C. Fred Rosenbaum
Assistant Examiner—John D. Ferros
Attorney, Agent, or Firm—Lackenbach, Siegel, Marzullo & Aronson

[57] ABSTRACT

A modular, portable water-jet system for attachment to the faucet of a kitchen or bathroom sink. The system includes a diverter valve assembly that can be screwed to the faucet and which has one outlet having an aerator and another outlet to which is removably attached a control valve assembly to which is removably attached a jet-flow device, such as an oral cleaning nozzle. The diverter valve assembly includes a spool valve slidably mounted in the housing. One end of the spool valve forms a passage from the inlet of the housing leading to the outlet port to the control valves assembly. A modular solution mixing and metering container can be optionally positioned between the diverter valve assembly and the control valve assembly when a liquid medicant or cleaning agent, for example, is desired. A cross-channel at the top of the container opens to the container where water mixes with and pressures the resulting mixture up a vertical pipe back to the cross-channel where it is pressured to the jet-flow device.

19 Claims, 18 Drawing Figures

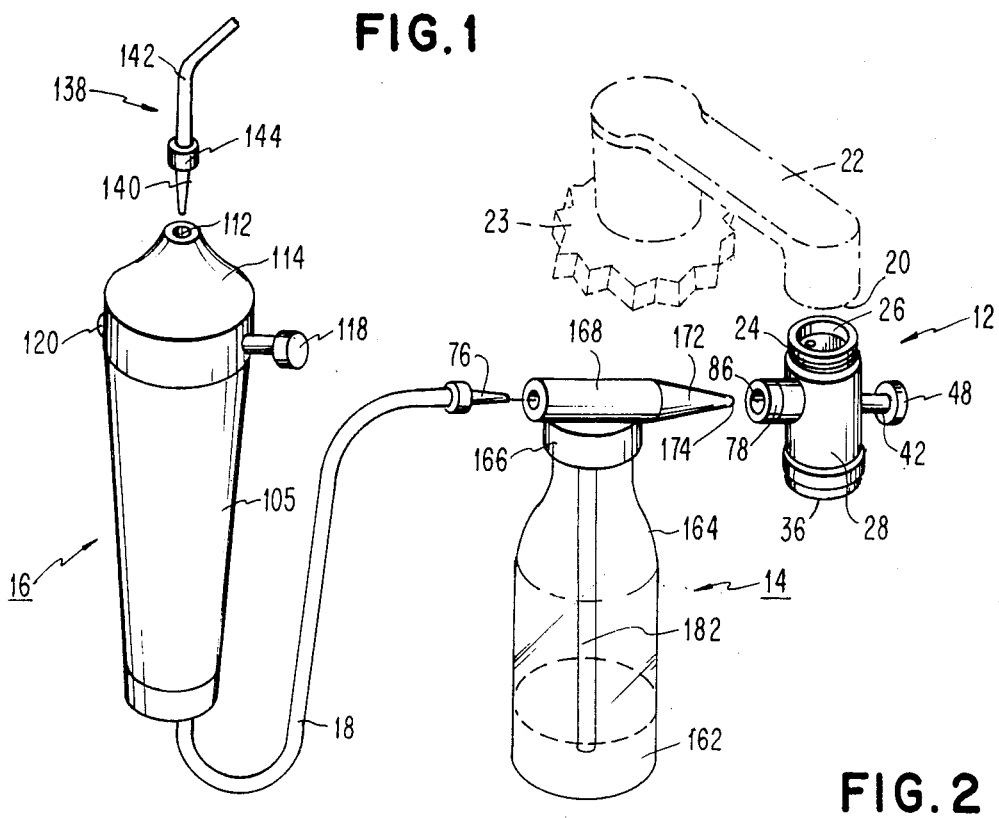
FIG. 1
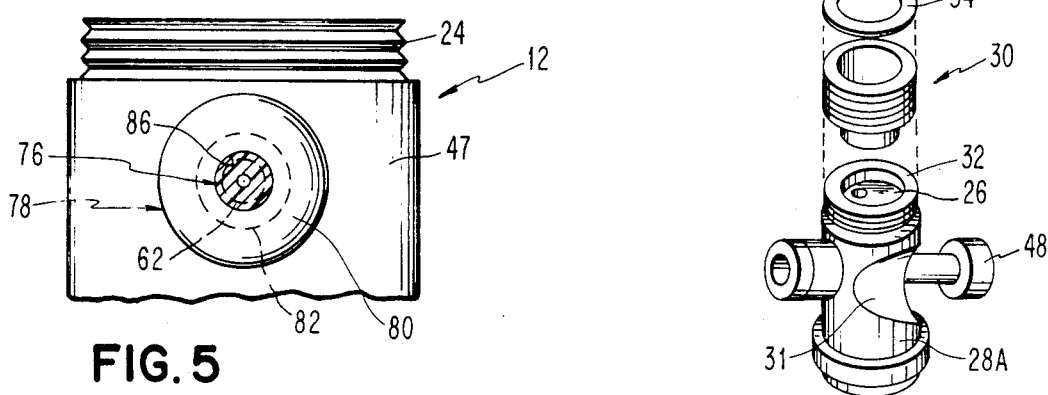
FIG. 2
FIG. 5
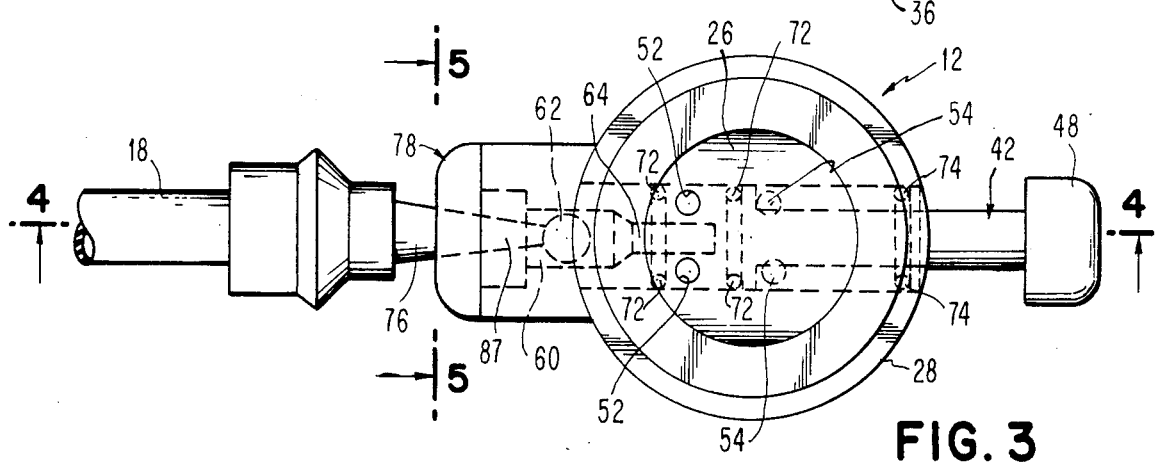
FIG. 3

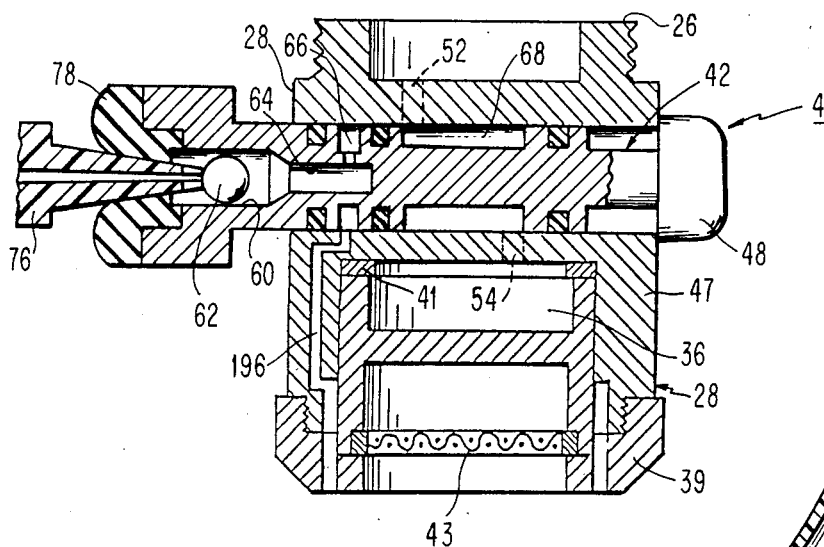
FIG. 7
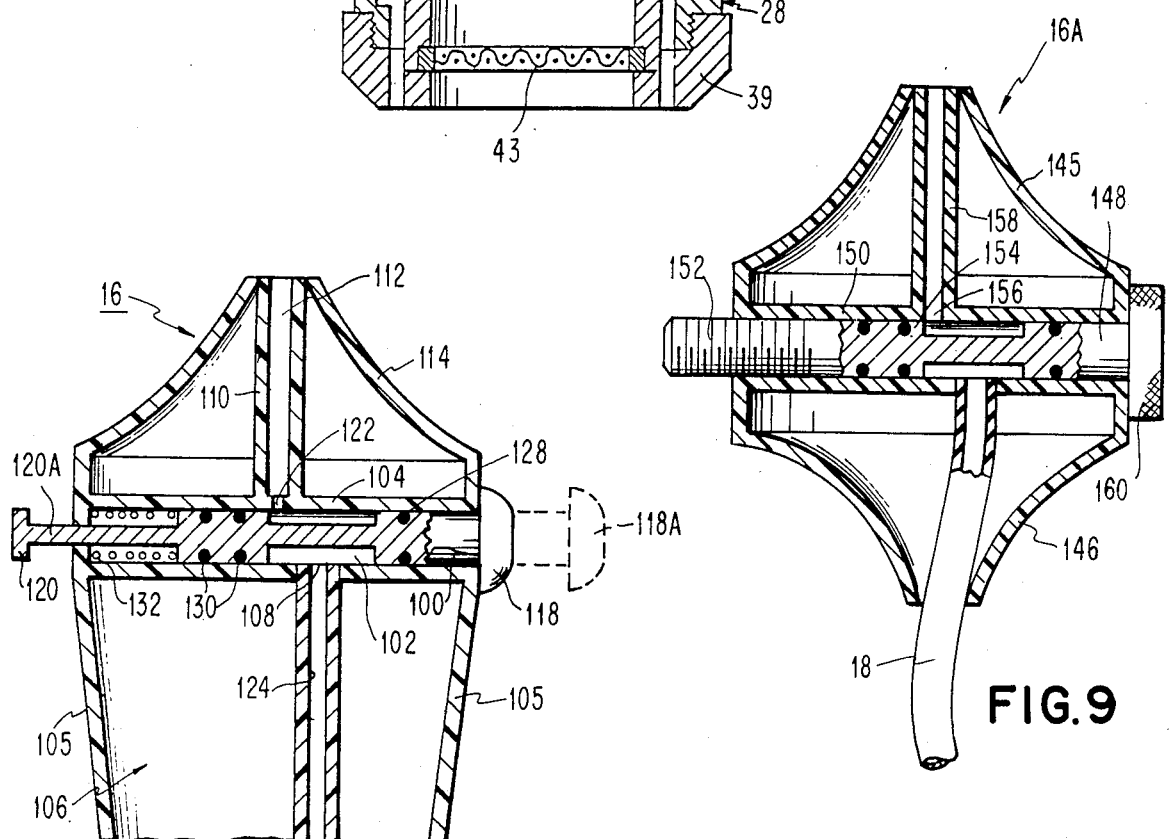
FIG. 9
FIG. 8
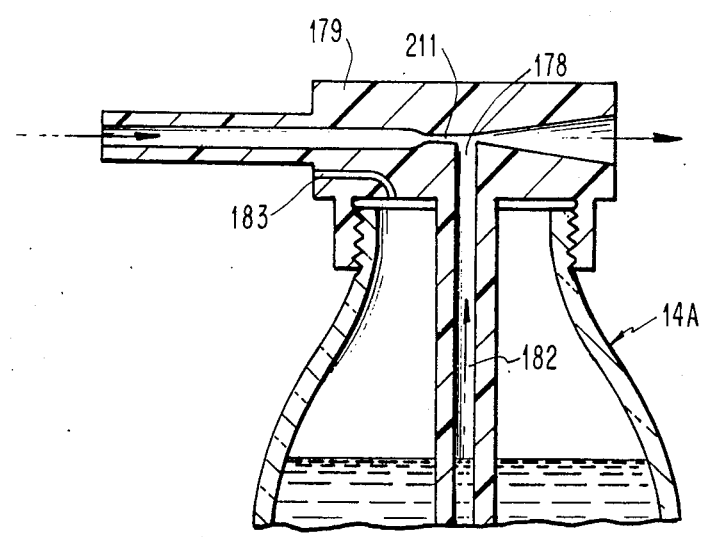
FIG. 15

PORTABLE WATER-JET SYSTEM

BACKGROUND OF THE INVENTION

This invention relates to a water-jet system that can be directed to uses such as personal hygiene and in particular to a modular portable system that can be attached to the faucet of a sink. Water-jet systems that can be attached to the faucet of a kitchen or bathroom sink, for example, are well-known. Despite their history of usage, in many areas they have defects which limit their uses. One defect of devices presently being marketed is that they are not adaptable to the varying statutory demands of certain states in the United States. One statutory requirement is that a jet system used with a medicated liquid solution must be provided with an anti-siphon attachment that prevents any medicant in the water-jet system from being sucked back into the drinking water lines in the event of a pumping or other type of failure that creates a vacuum in the water supply system. Separate attachments to the water-jet system being marketed is one method of meeting statutory requirements. This creates added cost.

Portable water-jet systems can be applied to a wide number of uses particularly if a medicant or chemical can be selectably introduced into the system. Additions of liquid medicants or cleansers include fluoride mixtures and bicarbonate of soda for oral water-jet cleansing; general anti-bacertia solutions for vaginal cleaning; general medicated or cleansing solutions for anal hygiene for hemmorrhoid sufferers, for example, and post-child birth and post-surgery requirements, during menstruation, and the like. Also, water-jets can be directed to other uses, such as watering and feeding plants, where liquid fertilizers can be introduced into the system in the same manner as hygiene solutions. In the present state of the art, no simple, easily mounted and inexpensive device is known that can accomplish these tasks.

SUMMARY OF THE INVENTION

Accordingly, it is an object of the present invention to provide a portable water-jet system that includes a diverter valve attachment that provides a pocket at the diverted outlet for the optional insertion of an anti-siphon ball.

It is also an object of the present invention to provide a water-jet system having a spool diverter valve having the diverted outlet axially formed in the spool valve with an enlarged pocket portion capable of optionally receiving an anti-siphon ball valve.

It is still another object of the present invention to provide a water-jet system having modular components that allow the inclusion of a container holding a liquid solution that can be metered into the jet-system.

It is yet another object of the present invention to provide a modular water-jet system that includes a container module for holding a liquid solution such as a medicant or chemical that holds a liquid that is churned by the water flow into a diluted liquid-water mixture that is gradually forced by water pressure into the jet-water line in steady increments that further dilute the mixture so that a steady application of the solution is effortlessly applied by the user to the desired objective.

In order to achieve the above objects, as well as others that will become apparent hereafter, a modular, portable water-jet system attachable to the faucet of a kitchen or bathroom sink is provided that includes a diverter valve assembly that comprises a water resistant housing, an inlet port formed by the housing removably connected to the faucet, a first outlet port formed by the housing generally appoints the inlet port, a passage formed by the housing for passing water from the inlet port to the outlet port; a second outlet port associated with the housing for passing water from the housing; a second passage formed in part by the housing for passing water from the inlet port to the second outlet port; and a spool valve positioned in a bore formed by the housing transverse to the first passage. The spool valve is movable between a first open position and a second open position, wherein in the first open position water is directed from the inlet port to the first outlet port and blocked from the second outlet port; and in the second open position water is diverted from the inlet port to the second outlet port and blocked from the first outlet port. The spool valve forms in part the second passage between the inlet port and the second outlet port. A female connecting hose is formed at the second outlet port. The spool valve forms a pocket associated with the second passage; the pocket is adapted to receive a ball for preventing backflow from the second outlet port to the inlet port in the event of a vacuum in the water supply lines. In addition, the ball blocks forward flow when the second outlet port is open.

A control valve assembly operatively connected directly to the diverter valve has connected to it a jet adapter that has a wedged nozzle connector slidably inserted into the outlet side of the control valve assembly. The jet adapter can be used for oral cleaning, for example. A plant watering wand, or a plant misting appliance, can be substituted for the oral cleaning appliance.

A solution mixing container can be optionally operationally inserted in the system between the diverter valve assembly and the control valve assembly. The solution can be a medicant or a cleanser as desired. In concentrated form it fills a portion of the container. The top of the container forms a cross-channel for passing tap water between the diverter valve assembly and the control valve assembly. An inlet from the channel to the container allows part of the incoming water to enter the container and fill it, mixing with the concentrated solution to form a fluid mixture. A vertical pipe extends in the container between the channel and to a position spaced from the bottom wall of the container. The pipe has a flow constrictor mounted in it. When the container fills with the mixed fluid, part of the mixture is metered through the flow constrictor in the pipe from the bottom of the pipe to the cross-channel where the mixture is forced into the cross-channel for further mixing with the pressured water and is sent to the control valve assembly and to the jet application.

The control valve assembly includes a spring controlled spool valve for selectively controlling water or mixture flow. Alternatively, the spool valve can be threadably controlled so that the valve can be screwed to the position that provides the optimum flow desired.

The container inlet connector includes a male connector insertable into the female connector of the valve assembly. A finger extends axially inwardly through an outer orifice downstream of the pocket of the valve assembly to a position upstream of the outer orifice wherein the ball is pressed free of the outer orifice so as to allow forward flow of the water. The finger forms an axial passage and opposed cutaway forming flow passages to the axial passage, which is fluidly connected to the male connector of the container. The same feature is provided for the male connector of the hose and valve control assembly when it is connected directly to the second outlet of the diverter housing.

BRIEF DESCRIPTION OF THE DRAWINGS

FIG. 1 is a perspective view of the modular water-jet system shown aligned for connecting:

FIG. 2 shows an alternate faucet attaching device for the diverter valve;

FIG. 3 is a top view of the diverter valve assembly;

FIG. 5 is an end view of the spool valve at the plug end;

FIG. 7 is a sectional view of the diverter valve similar to the view of FIG. 4 with the valve in a non-diverting position;

FIG. 8 is a sectional view of the control valve assembly with a biased spool valve;

FIG. 9 is a sectional view of the control valve assembly with a threaded spool valve;

FIG. 15 shows a sectional detail of the venturi tube used in a liquid fertilizer container.

DESCRIPTION OF THE PREFERRED EMBODIMENTS

Figure 4:
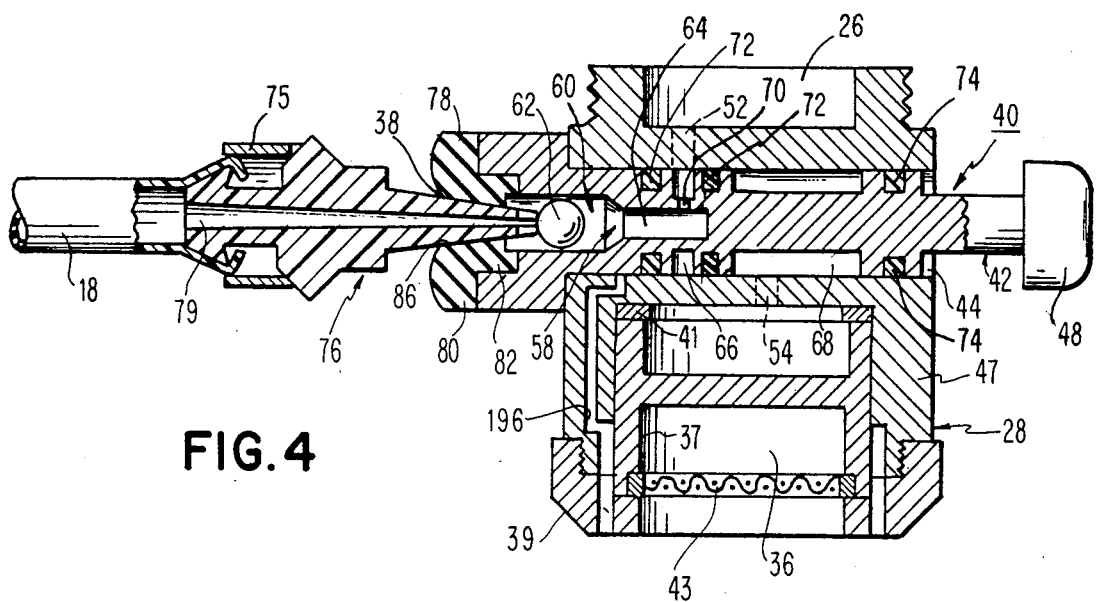
FIG. 4 is a sectional view of the diverter valve taken through line 4—4 of FIG. 3.

The invention will now be described in more detail with reference to the drawings A modular water jet system is shown in FIG. 1 in position for connection includes a diverter valve assembly 12, a solution mixing bottle, or container, 14, and a flow control valve assembly 16 connectable to container 14 by a connector hose 18. A jet adaptor, or appplicator, 138 is positioned for connection to the outlet side of control valve assembly 16. Diverter valve assembly 12 is positioned for screwing into the outlet port 20 of a faucet 22 of a kitchen or bathroom sink 23, for example. Outlet port 20 is provided with internal threads (not shown) that accept external threads 24 formed at the top inlet port 26 by diverter valve housing 28. FIG. 2 illustrates an alternative connecting method with a separate threaded adaptor 30 having upper external threads and lower external threads of lesser cross-diameter than the upper threads, with the upper threads screwable into outlet port 20 and the lower threads screwable into an inlet port 32 having internal threads. A washer 34 can be added at the top of threaded adaptor 30. Here, diverter valve assembly 12 has a housing 28A having pinched sides 31 that aid in the handling of the assembly by a user.

FIGS. 3 and 4 show diverter valve assembly 12 in detail. Housing 28, which is made of a water-resistant material and preferably chrome-plated, forms a first outlet port 36 opposite inlet port 26. An aerator 37 is mounted to outlet port 36 and is held in place by a screw lock 39. A washer 41 is inserted between the top of the aerator and the inner side of first outlet port 36. A screen 43 disposed across the bottom of first outlet port 36 is also held in place by screw lock 39.

A spool valve 40 is slidably mounted in housing 28. In particular, spool valve 40 includes an elongated cylinder 42 that is slidably mounted in a cylindrical bore 44 formed by an internal wall 46 of housing 28 transverse to the flow of water from inlet port 26 to first outlet port 36 and transverse to cylindrical side walls 47 of housing 28. Cylindrical member 42 has a handle 48 at one end and a cap, or plug, member 78 secured by gluing or heat sealing at the opposite end which forms a second outlet port 38 situated transverse to inlet port 26 and outlet port 36. Both handle 48 and plug 78 are positioned outside of side wall 47 of housing 28 with cylinder member 42 extending through apertures 44 in wall 47. Cylinder member 42 is flattened at the point it extends through wall 47 in order to prevent rotation of the cylinder member. Internal wall 46 forms a pair of ports, or holes, 52 between inlet port 26 and bore 44 and also forms a pair of outlet ports, or holes, 54 between bore 44 and first outlet port 36.

Cylinder member 42 forms an axial passage 58 between plug 78 and a position axially spaced from plug 78. Axial passage 58 includes a cylindrical pocket 60 adapted to hold a valve ball 62, with the diameter of pocket 60 being greater than the diameter of ball 62 so as to allow the passage of water around ball 62 in a downstream direction. Cylindrical pocket 60 is sufficiently long to allow ball 62 movement along the pocket. Axial passage 58 includes a cylindrical passage 64 disposed upstream of pocket 60.

Passage 64 is smaller in diameter than ball 62 so that ball 62 will block passage 64 if water flow reverses and ball 62 is pressed against the port connecting passage 64 with pocket 60 so that the port is blocked and reverse flow is stopped. The port connecting passage 64 with pocket 60 is tapered so as better to seat ball 62 in a blocking position.

Cylinder member 42 also forms a pair of outer, open first and second circular passages 66 and 68. First circular passage 66 is radially spaced from axial cylindrical passage 64. Cylinder member 42 further forms an inlet aperture, or port, 70 between passage 64 and first circular passage 66. Second circular passage 68 is axially spaced from first circular passage 66 towards handle end 48.

Spool valve 40 is movable between diverting and non-diverting positions. In the diverting position cylinder member 42 is positioned so that first circular passage 66 is aligned with inlet port 52, wherein flow is directed from inlet port 26 into first circular passage 66 through inlet hole 52 into inlet port 70 and axial passage 64 to second outlet port 38. In the non-diverting position cylinder member 42 is positioned so that said second circular passage 68 is aligned with inlet port 26 and with outlet hole 54, wherein flow is directed from inlet port 26 through a pair of inlet holes 52 into second circular passage 68 through a pair of outlet holes 54 and outlet port 36. A pair of O-rings 72 are positioned in circular grooves formed in cylinder member 42 on either side of first circular passage 66 and an O-ring 74 is positioned in a circular groove formed in cylinder member 42 on the handle side of second circular passage 68.

Figure 4A:
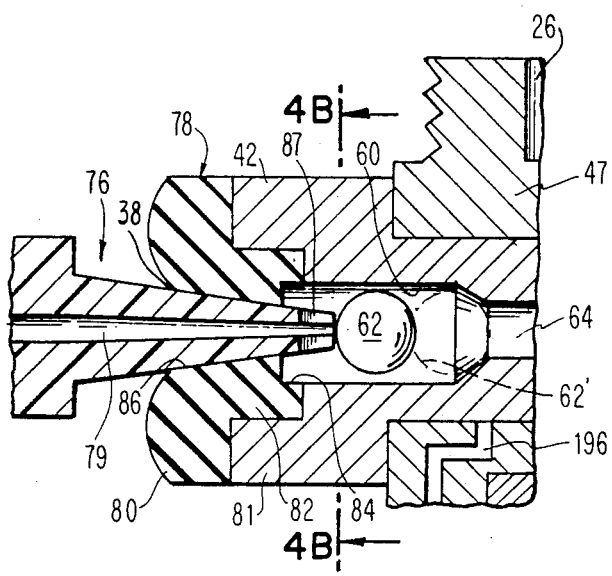
FIG. 4A is an isolated sectional view of an alternate embodiment of the ball valve shown in FIG. 4.
Figure 4B:
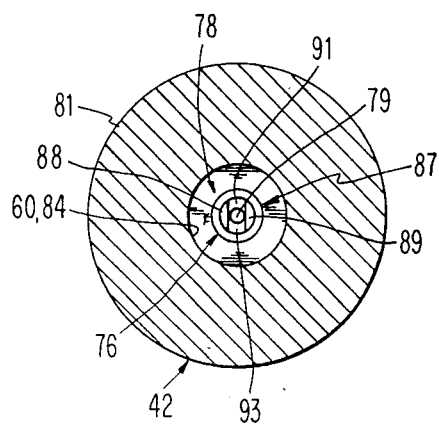
FIG. 4B is an end view of the needle of the nozzle of the adapter.
Figure 6:
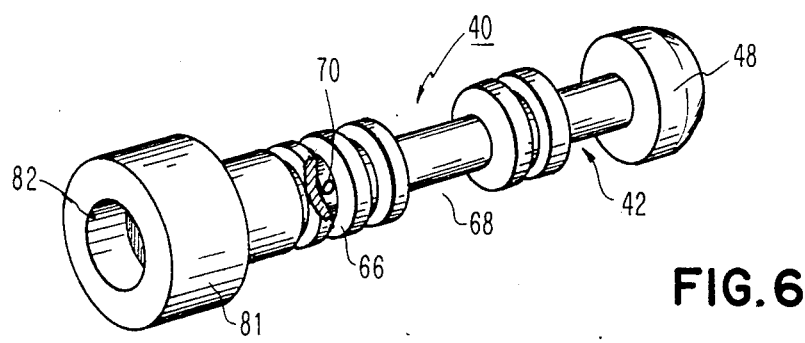
FIG. 6 is an isolated isometric view of the cylindrical member of the spool valve.

As shown in FIGS. 3, 4, and 4B, connector hose 18 is held by a hose retaining ring 75 onto an adaptor provided with a tapered male nozzle connector 76 forming a cylindrical bore 79. Nozzle connector 76 is slidably inserted into female socket member 78 that is made integral with cylinder member 42 by gluing or other method known in the art after insertion of ball 62, pocket 60 and mounting onto the mounting end of cylindrical member 42. Socket member 78 includes an outer concentric disk portion 80 and an inner disk portion 82 having a smaller diameter than outer disk portion 80. Socket member 78 forms an axial cylindrical socket bore 86 adapted to accept male nozzle connector 76. Bore 86 and bore 79 are axially aligned. Inner disk portion 82 forms a cylindrical pocket 84 that is coextensive with pocket 60 and co-axial with bore 86. Pocket 84 is smaller in diameter than bore 86. As seen in FIGS. 4, 4A, and 4B, a needle, or finger, 87 connected to the tip of the nozzle of adaptor 76 extends into pocket 84 when the adapter 76 is connected directly to outlet 86 of diverter assembly 12. Finger 87 acts as a stop to prevent ball 62 from closing off bore 86 and nozzle bore 79 when flowing water has pushed ball 62 downstream as shown in FIG. 4A in solid line from a non-pressing position shown as 62' in phantom lines. Nozzle 76, which has been press-fitted into bore 86, is firmly in place in bore 86 to the extent to resist the downstream pressure exerted by the water flow against nozzle 76 at finger 87. In the event that nozzle 76 is pushed from socket member 78 by the water pressure, ball 62 will quickly be pushed against bore 86 so as to close off the water flow and, by so doing, to prevent water from squirting from diverter valve assembly 12. This same feature prevents water from squirting from valve assembly 12 in the event a user inadvertently pulls nozzle 76 from socket member 78 without first shutting off the faucet valve.

Finger 87, includes a pair of inwardly extending opposed arms 88 and 89, seen in FIG. 4B, that are spaced apart so as to clear socket bore 79. A pair of opposed cutouts 91 and 93 are formed by finger 87 at right angles to arms 88 and 89 forming flow channels adapted to pass flow to socket passage 79. Ball 62 is loose enough in pocket 84 that water flows around the ball and between arms 88 and 89 and into socket passage 79.

FIGS. 3 and 4 show spool valve 40 in its diverting mode aligned with handle 48 being pulled back from side wall 47 of housing 28 so that first circular passage 66 is aligned with the pair of inlet holes 52 to allow passage of water through inlet port 70, passage 64, pocket 60, passage 86 of socket member 78 to the bore 79 of tapered nozzle 76 positioned in the end of second outlet port 38. Spool valve 40 is shown in its non-diverting mode in FIG. 7 with handle 48 pressed against wall 47 of housing 28 and second circular passage 68 now aligned with inlet holes 52 and outlet holes 54 to first outlet port 36 with passage of water to hose 76 blocked.

Modular water jet system 10 can be assembled with control valve assembly 16 connected directly to diverter valve assembly 12 as described in FIGS. 3, 4 and 7, or, as shown in FIG. 1, be connected to intervening mixing container 14. As seen in FIG. 8, control valve assembly 16 includes a spool valve having a cylinder member 100 slidably mounted in a cylindrical bore 102 formed by an internal wall 104 connected to a housing, or enclosure, 105. Connector hose 18 has its inlet upstream end connected to adaptor 76 and its outlet downstream end 108 in flow connection with bore 102 preferably transverse to bore 102 slightly offset from the transverse center of the bore. A rigid tube 110 extends from bore 102 from the transverse center of the bore, that is, slightly offset from downstream end 108 of hose 18 and generally in extended parallel relationship with the incoming line of hose 18. Enclosure 106 is preferably of a stiff plastic and extends to a plane spaced past internal wall 104. A conical support 114 of rigid plastic connected to enclosure 106 extends from a base at the ends of inner wall 104 and rising gradually to outlet end 112. Enclosure 106 further extends from the ends of inner wall 104 opposite tube 110 in an extended tapered cylinder adapted to being held by an operator terminating at a base wall 116 through which hose 18 extends. Cylinder member 100 has a handle 118 at one end and a stop button 120 at the opposite end, both positioned outside the walls of enclosure 106. Inner wall 104 forms a first hole 122, which is the inlet port for tube 110 and an offset second hole 124, which is the outlet port for hose 18. Cylinder member 100 forms a circular open passage 126 between its axial central portion and inner wall 104 in bore 102. As seen in FIG. 8, circular passage 102 opens to both off-center inlet hole 124 and center outlet hole 122. An O-ring 128 is positioned on the handle 118 side of cylinder member 100, and a pair of O-rings 130 on the opposite, or stop button 120 side of the cylinder member. Both handle 118 and stop button 120 are greater in diameter than the apertures in wall 105 through which cylindrical member 100 slides. A coil compression spring 132 is slidably disposed in bore 102 around the axial stem of cylindrical member 100. Spring 132 is braced between side wall 105 and a circular shoulder 134 of cylindrical member 100 positioned on the stop button side of O-rings 130. The spool valve of control valve assembly 16 is movable to a plurality of intermediate positions between and including a fully open and a fully closed position. In the fully open position cylindrical member 100 is positioned as shown in FIG. 8 with handle 118 being positioned against side wall 105 and stop member 120 being spaced away from side wall 105 so that spring 132 is in its fully biased mode and bore 102 becomes a passage aligned with both first and second holes 122 and 124 and water from hose 18 feeds fully to tube 110. In the fully closed position generally indicated in FIG. 8 by phantom lines for stop member 120A and handle 118A, cylindrical member 100 is positioned with handle 118 spaced from enclosure wall 106 and stop member 120 pressed against side wall 105 with spring 132 being extended to its unbiased mode. A cylindrical blocking portion 136 of cylinder member 100, shown as 136A in phantom lines, positioned between the pair of O-rings 108 is set across first hole 122 so that water flow is fully blocked from tube 110. Blocking portion 136 can be maneuvered so as to block first hole 122 at a plurality of positions in allowing selective amounts of flow to tube 110.

FIG. 1 illustrates a jet adaptor 138 having a wedge nozzle 140 about to be inserted into outlet 112 of tube 110 (FIG. 8) of control valve assembly 16. The jet outlet tube 142 is bent slightly and is intended for the purpose of oral cleansing. A mounting ring 144 is preferably set around adaptor 138 for storing to a mounting bracket (not shown) and for gripping for removal of tube 142 from outlet end 112.

FIG. 9 illustrates a control valve assembly 16A similar to control valve assembly 16 shown in FIG. 8 except that the handle portion of enclosure 106 has been substituted by a conical support 146 the reverse image of conical support 145, which in turn is similar to conical support 114 of FIG. 8. Flexible hose 18 is bent inside of conical support 146 to enable it to pass through the center of the conical support. Cylinder member 148 and inner wall 150 are provided with mating threads 152 to enable cylinder member 148 to be screwed and positioned at one of the plurality of open positions.

Cylinder member 148 is shown with blocking portion 154 blocking about one-half of inlet hole 156 to tube 158. Handle 160 is adapted to being rotated rather than being pushed. Control valve assembly 16A is employed where the flow desired is known and can be permanently set in advance of use and to facilitate a more precise control.

Figure 10:
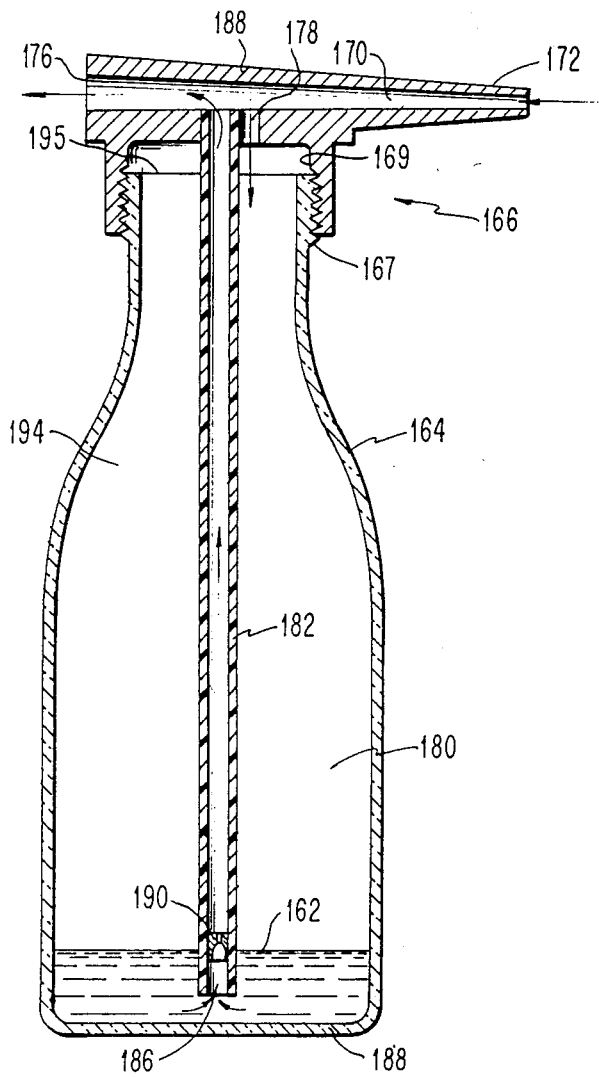
FIG. 10 is a sectional view of the solution mixing container.

FIG. 10 illustrates in detail the solution mixing container 14 shown in FIG. 1. There are a number of uses for the jet system that would require, or at least find useful, a device that would introduce a medicated liquid or cleansing solution into the jet spray. For oral cleaning, a bicarbonate of soda and peroxide solution or a fluoride mixture can be made. The solution can be placed in the container in concentrated form and then is diluted and forced into the line by water pressure in the container. The concentrated solution is thus in effect metered into the flow of water.

As shown in FIG. 10, a concentrated liquid solution 162 of the nature of the liquid solutions described in the paragraph above, is shown in its concentrated form by a phantom line at the bottom portion of a container, here a plastic bottle, 164. A cap 166 is removably connected by threaded connector 167 onto the top of bottle 164. The cap seals an access aperture 169 at the top of the bottle. A mounting 168 integral with and over cap 166 forms a transverse channel 170 over the top of cap 166.

A male wedged connecting nozzle 172 extending from mounting 168 forms an extension of channel 170. Channel 170 has an inlet end 174 at the nozzle end of the channel and an outlet end 176 at the opposite end of the channel.

A finger 177 the same in arrangement and design as finger 87 discussed in relation to FIG. 4A extends axially outwardly from the tip of inlet end 174. Finger 177 forms a pair of opposed cutouts forming flow channels to channel 170. Finger 177 acts to press ball 62 away from the orifice of bore 86 at second outlet port 38 leading into pocket 60. If bottle 164 with nozzle 172 is withdrawn from bore 86 before the faucet is shut, ball 62 is pressed downstream in pocket 60 to shut off bore 86 from water flow.

Figure 11:
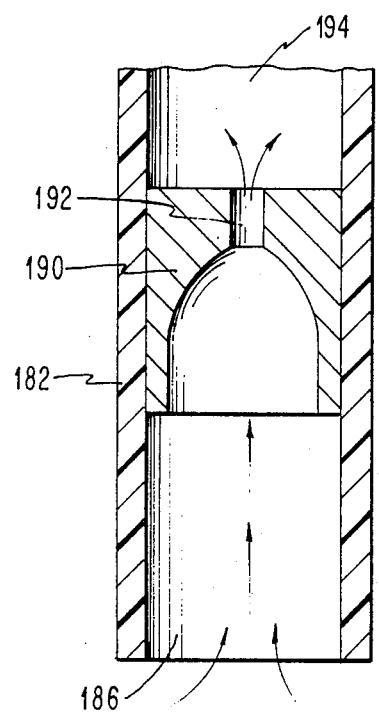
FIG. 11 is an isolation view of the flow restrictor of the mixing container.

Cap 166 forms an inlet hole 178 that joins channel 170 with volume 180 formed by the walls of bottle 164. An elongated pipe 182 is connected to cap 166 and is fluidly connected to channel 170 at an outlet 184 at the center of cap 166 directly downstream of inlet hole 178 and extends vertically downwardly in bottle 164 to an inlet 186 spaced relatively close to bottom wall 188 of bottle 164. The fill line of solution 162 is shown to be above inlet 186, but this is not necessary to the operation of the container. A flow restrictor 190 is positioned in pipe 182 preferably near inlet 186 as shown in FIGS. 10 and 11. Flow restrictor 190 narrows the area of flow to a constricted passage 192.

Connector nozzle 172 is adapted to be accepted in removable wedged connection by socket bore 86 of cylinder member 42 of diverter valve assembly 12 at the option of the user, as indicated in FIG. 1. Tapered adapter nozzle connector 76 is adapted to be inserted into outlet 176 of channel 170 of cap 166 and held in removable gripping relationship therein.

In operation, water will flow from diverter valve 12 into inlet 174, through channel 170 to inlet hole 178. At that point water flow will move in two directions: one portion of the water flow will continue through channel 170 to outlet 176 to hose 18 and central valve assembly 16; another portion of water flow will pass into volume 180 of bottle 164 into a mixing action between the inflowing water and concentrated solution 162 at the bottom of the bottle. Solution 162 and the water will combine to form a mixture 194 which will almost fill volume 180 almost to the top of the bottle as shown by a solid line 195 in FIG. 10. When the bottle has been filled with mixture 194, further pressure by water inflow at inlet hole 178 will force mixture 194 into inlet 186 of pipe 182 and through flow constrictor 190 and up pipe 182 to outlet 184 where mixture 194 joins and further mixes with the water flow portion coming directly from diverter valve 12 to form a diluted mixture (not shown as a separate numeral) to control valve assembly 16 and application as directed by the user. In this manner, the total amount of concentrated solution 162 is known before attaching mixing container 14 to the system.

When the system has been in operation with water flow being diverted in full flow at diverter valve assembly 12, the proper procedure to stop operation is first to turn off flow from the faucet at the faucet sink valve (not shown), then to pull spool valve 40 back from its diverting mode to its non-diverting mode. If, however, the user inadvertently first pulls spool valve 40 to its non-diverting mode first, a considerable buildup of water pressure will remain in the system with water in the amount of hose 18 being used in the system. In such a case, disconnection of the system can result in water bursts. In order to eliminate such an occurrence, a pressure relief line 196 as shown in FIGS. 4 and 7 is formed by housing 28 at side wall 47 of diverter valve assembly 12. Pressure relief line 196 opens to the atmosphere adjacent to first outlet port 36 at one end and opens at its inner end to first circular passage 66 of cylindrical member 42 of spool valve 40 as seen in FIG. 7 when the spool valve is in its non-diverting mode. The system will be allowed to relieve itself of pressure upon movement of cylinder member 42 to the non-diverting position shown in FIG. 7 in the event water flow from faucet 22 has not been turned off previously. A small quantity of water will then flow from the line pushing water in pocket 60 or cylindrical passage 64 to circular passage 66 and from the system at pressure relief line 196. It will be appreciated that only a very small amount of water will pass from the system at pressure relief line 196 in order to relieve the system. When spool valve 40 is moved to its diverting mode as seen in FIG. 4, pressure relief line is closed off at its inner end by the outer wall of cylinder member 42.

Figure 12:
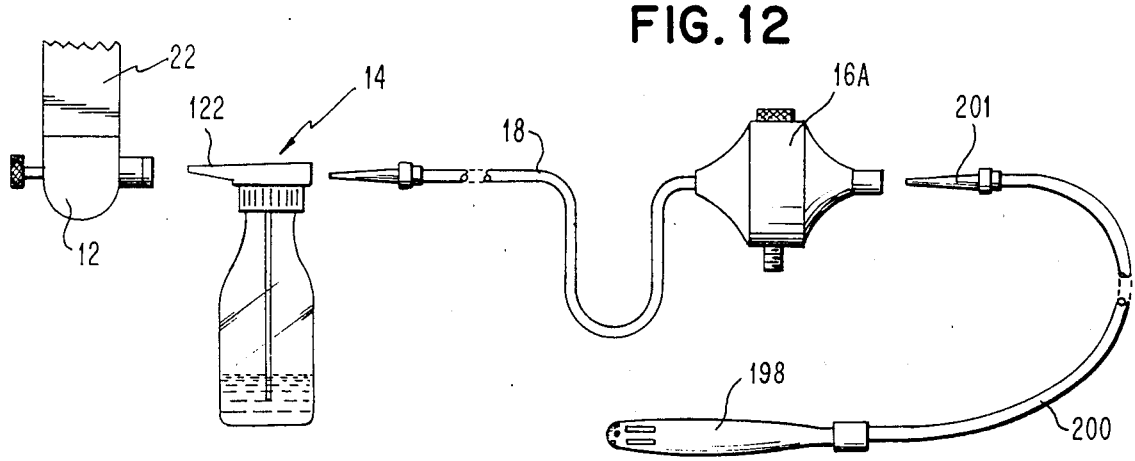
FIG. 12 illustrates the water jet system used with a vaginal cleansing pipe.
Figure 13:
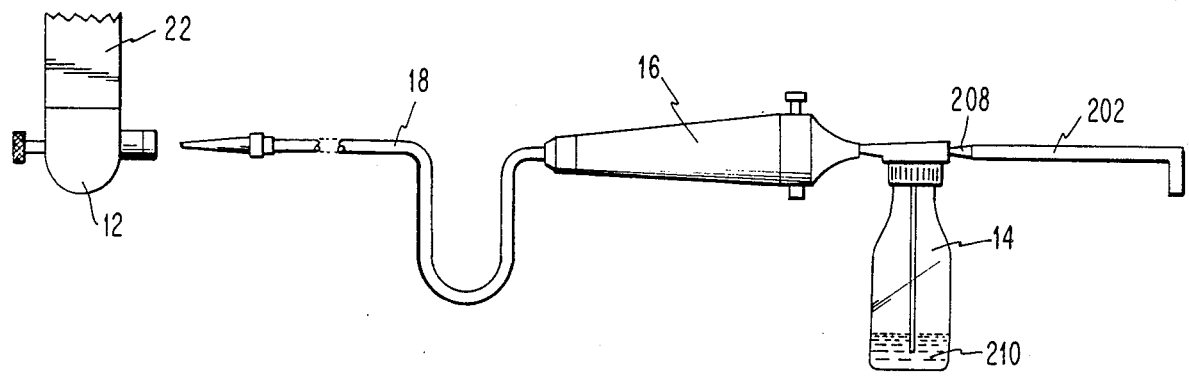
FIG. 13 illustrates the water-jet system used with a plant watering wand.
Figure 14:
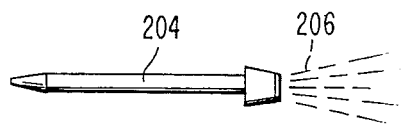
FIG. 14 shows a plant misting appliance capable of being used with the water-jet system shown in FIG. 13.

FIGS. 12, 13 and 14 illustrate alternate applications of the water jet system in addition to the dental cleaning application shown in FIG. 4.

FIG. 12 illustrates the jet system applied to a douche bone, or vaginal pipe, 198, which is attached to a connecting hose 200 having a tapered nozzle converter 201 adapted to be fitted to the outlet end of a control valve assembly 16A similar to the embodiment shown in FIG. 9 where a threaded adjustor 152 for the spool valve is shown. Hose 18, optional solution mixing container 14, and diverter valve assembly 12 attached to faucet 22 are as previously described.

FIGS. 13 and 14 illustrates a jet system applied to a house plant watering and feeding watering wand 202, or, in place of the watering wand, a misting attachment 204 as shown in FIG. 14 which shows mist 206 spraying from the end of the attachment. Watering wand 202 (or misting attachment 204) is directly attached by way of a tapered nozzle connector 208 to optional mixing container 14A, which contains a liquid plant feed 210 to be metered to the plants, which is in turn attached to a control valve assembly 16 as shown in FIG. 8. Hose 18 is long, approximately 50 feet, and is joined to diverter valve assembly 2 in turn screwed into faucet 22.

FIG. 15 illustrates a detail view of mixing container 14A particularly the venturi constriction 211 at hole 178 in pipe 182. The screw cap 179 is provided with a vent hole 183 permitting the atmosphere to enter container 14A and act on the liquid solution 180 in container 14A. Thus, with the venturi restriction 211, as the flow increases in the venturi 211 (caused by the constricted passageway size), the pressure at hole 178 is reduced and made lower by the quickly moving fluid flowing past the hole 178. This action thereby caused the liquid solution in container 14A to flow into the pipe 182 and into venturi passageway 211 and thus to be mixed with the fluid flow.

Figure 16:
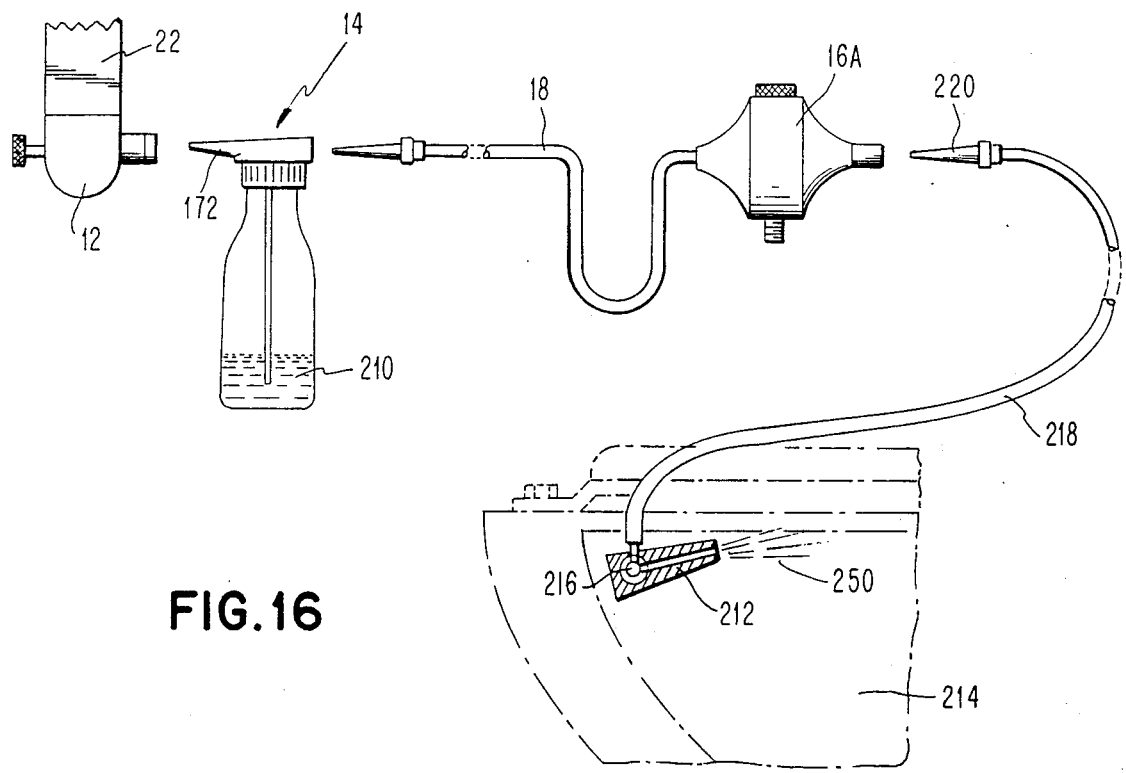
FIG. 16 illustrates the water-jet system used with an anal cleansing device.

FIG. 16 illustrates the water-jet system as applied to an anal cleansing appliance 212 at the rear of a toilet bowl 214 positioned to be used as an anal jet. Anal cleansing appliance is positioned by a horizontal rigid tube 216 that is connected to a hose 218 that in turn is adapted to be connected to a control valve assembly 16A having a threaded valve as shown in FIG. 9 via a wedged nozzle connector 220. Hose 18 connects control valve assembly 16A to optional mixing container 14, which contains a liquid medicated or cleanser solution. Container 14 is adapted to be connected by its nozzle 172 to diverter valve assembly 12 in turn screwed into faucet 22. Appliance 212 provides a super narrow water stream jet 250 directed only to the anal area.

The embodiment of this invention particularly disclosed and described herein above is presented merely as an example of the invention. Other embodiments, forms, and modifications of the invention coming within the proper scope and spirit of the appended claims will, of course, readily suggest themselves to those skilled in the art.

What is claimed is:

1. A modular water-jet system for attachment to the faucet of a water outlet, compromising, in combination,
  a water-resistant diverter housing,
  inlet means formed by said housing removably connected to the faucet for passing water from the faucet to said housing,
  valve means positioned in said housing for directing water from said inlet means,
  first outlet means formed by said housing adapted to pass water from said housing,
  first passage means formed by said housing for passing water from said inlet means to said first outlet means,
  second outlet means associated with said housing and said valve means for passing water from said housing,
  second passage means formed by said valve means for passing water from said inlet means to said second outlet means,
  said valve means being movable between a first open position and a second open position, wherein in said first open position water is directed from said inlet means to said first outlet means and blocked from said second outlet means, and in said second open position water is diverted from said inlet means to said second outlet means and blocked from said first outlet means,
  said valve means being a spool valve having an elongated cylinder member having a handle end and an opposed mounting end, both said handle end and said mounting end being positioned external to said housing, said housing having an internal wall forming a bore, said cylinder member being slidably movable in and in sealing relationship with said bore, said first passage means including said internal wall forming at least one inlet hole between said inlet means and said bore and at least one outlet hole between said bore and said first outlet means, wherein said first passage means is said inlet side hole, said bore, and said outlet side hole, said cylinder member forming an axial passage between said second outlet means and a position axially spaced from said second outlet means, said cylinder member also forming a first outer circular passage radially spaced from the axis of said cylinder member, said cylinder member also forming an inlet aperture joining said axial passage and said first outer circular passage, said cylinder member also forming a second outer circular passage axially spaced from said first outer circular passage towards said handle end, said spool valve being operable between diverting and non-diverting positions, wherein in said diverting position said cylinder member is positioned so that said first outer circular passage is aligned with said at least one inlet hole so as to create said first passage means, and wherein is said non-diverting position said cylinder member is positioned so that said second outer circular passage is aligned with said at least one inlet hole and said at least one outlet hole so as to create said second passage means, said axial passage including an inner passage portion, said cylindrical member forming an inlet port between said inner passage portion and said first circular passage, said axial passage also including a cylindrical pocket downstream of said inner passage portion, a ball member having a smaller diameter smaller than the diameter of said cylindrical pocket being positioned in said cylindrical pocket, said cylindrical pocket having an axial length adapted to allow axial movement of said ball member, said cylindrical member forming a constricted passage having a downstream orifice downstream of said pocket, said second outlet means opening to said constricted passage, said contricted passage being of greater diameter than said ball member, wherein when said ball valve is spaced from said contricted passage water can flow through said pocket around said ball member through said second outlet means, and when said ball valve is positioned against said downstream orifice by the force of flow of the water, the water is prevented from flowing through said contricted passage and said second outlet means.

2. A system according to claim 1, further including anti-backflow means for preventing backflow from said second outlet means through said inlet means, said anti-backflow means including said axial passage having an upstream orifice between said inner axial portion and said pocket, said upstream orifice being cylindrical and having a smaller diameter than said ball member, said ball member being adapted to close off said upstream orifice and thus prevent backflow from said second outlet means to said inlet means.

3. A system according to claim 1, further including control means for receiving flow from said second outlet means of said housing, discharging the flow, and controlling the rate of discharge of the flow.

4. A system according to claim 3, wherein said control means includes a control valve, a hose having an upstream end connector adapted to be removably placed in operative flow connection with said second outlet means and a downstream end connected to said control valve, and a rigid tube having an outlet end and an opposed inlet end connected to said control valve, said control valve being movable to a plurality of intermediate selected positions between and including a fully open position and a fully closed position, wherein in said fully open position water from said hose is fully passed to said inlet end of said tube and in said fully closed position water from said hose is fully blocked from said inlet end of said tube.

5. A system according to claim 4, wherein said upstream end connector of said blocking includes hose means for keeping said ball member free from said downstream orifice.

6. A system according claim 5, wherein said blocking means includes said upstream end connector of said hose being a male connector and said second outlet means being a female connector, said male connector including a finger extending axially inward through said second orifice to a distance upstream of said second orifice wherein said ball member is pressed free of said second orifice, said finger forming an axial channel and opposed cutaways forming flow passages to said axial channel, said axial channel being fluidly connected with said male connector.

7. A system according to claim 4, further including enclosure means for mounting said control valve and said tube.

8. A system according to claim 7, further including container means directly connected to said second outlet means, said container means being for holding a liquid concentrated solution for mixing with the flow of water received upstream from said outlet means and having the resulting mixture sent downstream to said upstream end of said hose.

9. A system according to claim 8, wherein said container means includes a container having a bottom wall, said container forming a closed volume and an aperture opposite said bottom wall; cap means for removably sealing said aperture; channel means integral with said cap means having an inlet portion and an opposed outlet portion, said cap mean forming a small hole to said channel means opening to said volume; an elongated pipe connected to said cap means and positioned in said volume and having one end opening to said channel means downstream of said small hole and an opposed open end spaced from said bottom wall; a container inlet connector integral with said cap means positioned at said inlet portion adapted to be removably mounted to said connecting means at said second passage means; and a container outlet connector integral with said cap means at said outlet portion adapted to be removably mounted with said upstream end of said hose of said control valve means; said liquid concentrated solution being disposed in said container.

10. A system according to claim 9, wherein said container inlet connector includes blocking means for keeping said ball free from said second orifice.

11. A system according to claim 10, wherein said blocking means includes said container inlet connector being a male connector and said second outlet means being a female connector, said male connector including a finger extending axially inwardly through said second orifice to a position upstream of said second orifice, said finger forming an axial channel and opposed cutaways forming flow passages to said axial channel, said axial channel being fluidly connected with said male connector.

12. A system according to claims 6 or 11, further including a pressure relief line formed in said housing between the atmosphere proximate to said first outlet means and said bore at a position opening to said first outer circular passage when said cylinder member is in said second open position, whereby water under pressure in the system downstream of said second outlet means is relieved through said pressure relief line.

13. A system according to claim 9, wherein said male connector of said container is removably mounted to said second outlet means and said downstream end of said hose of said control means being a hose male connector, said hose male connector being removably connected to said female outlet connector of said container.

14. A system according to claim 13, wherein said container is removably mounted to said connecting means at said second outlet means and said downstream end of said hose of said control means being a hose male connector, said hose male connector being removably connected to said female outlet connector of said container.

15. A system according to claim 14, further including application means removably connected to said outlet end of said tube of said control means, said application means being for directing the flow of mixture received from said tube to a selected object.

16. A system according to claim 15, wherein said channel means has a constricted venturi passage means at said pipe for restricting the flow so as to create a jet flow from said outlet portion.

17. A system according to claim 15, wherein said application means includes a male connector adapted to be slidingly received by said discharge end of said tube of said control valve and opposed spray nozzle adapted to direct a jet spray at an object such as teeth.

18. A system according to claim 15, wherein said application means includes an anal jet member positioned in another toilet and a tube connected to said outlet end of said control valve means.

19. A system according to claim 13, wherein said container means is positioned downstream of said control means, said hose male connector being removably connected to said outlet end of said tube of said control means.

* * * * *